US009458433B2

(12) United States Patent
Lischka et al.

(10) Patent No.: US 9,458,433 B2
(45) Date of Patent: Oct. 4, 2016

(54) PRODUCTION OF DENSE BODIES (DB) FROM HCMV-INFECTED CELLS

(75) Inventors: Peter Lischka, Duesseldorf (DE); Christian Sinzger, Reutlingen (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 57 days.

(21) Appl. No.: 14/116,814

(22) PCT Filed: May 3, 2012

(86) PCT No.: PCT/EP2012/058094
§ 371 (c)(1),
(2), (4) Date: Mar. 4, 2014

(87) PCT Pub. No.: WO2012/152644
PCT Pub. Date: Nov. 15, 2012

(65) Prior Publication Data

US 2014/0178432 A1 Jun. 26, 2014

(30) Foreign Application Priority Data

May 10, 2011 (DE) ........................ 10 2011 101 446

(51) Int. Cl.

| | |
|---|---|
| ***C12N 7/00*** | (2006.01) |
| ***A61K 39/12*** | (2006.01) |
| ***A61K 39/245*** | (2006.01) |
| ***C07D 239/84*** | (2006.01) |
| ***C07D 401/04*** | (2006.01) |
| ***C07D 401/12*** | (2006.01) |
| ***C07D 413/04*** | (2006.01) |
| *A61K 39/00* | (2006.01) |

(52) U.S. Cl.
CPC ................. *C12N 7/00* (2013.01); *A61K 39/12* (2013.01); *A61K 39/245* (2013.01); *C07D 239/84* (2013.01); *C07D 401/04* (2013.01); *C07D 401/12* (2013.01); *C07D 413/04* (2013.01); *A61K 2039/5258* (2013.01); *C12N 2710/16134* (2013.01); *C12N 2710/16151* (2013.01)

(58) Field of Classification Search
CPC .................. A61K 2039/5258; A61K 31/517; A61K 31/5517; A61K 39/12; A61K 39/245; C07D 239/84; C07D 401/04; C07D 401/12; C07D 413/04; C12N 2710/16134; C12N 2710/16151; C12N 7/00
See application file for complete search history.

(56) References Cited

U.S. PATENT DOCUMENTS

| | | | |
|---|---|---|---|
| 7,196,086 B2 | 3/2007 | Wunberg et al. | |
| 8,513,255 B2 | 8/2013 | Wunberg et al. | |
| 2005/0065160 A1 | 3/2005 | Wunberg et al. | |
| 2007/0191387 A1 | 8/2007 | Wunberg et al. | |
| 2011/0008387 A1 | 1/2011 | Grode | |
| 2013/0028935 A1 | 1/2013 | Grode | |
| 2013/0045230 A1 | 2/2013 | Grode | |
| 2013/0202708 A1* | 8/2013 | Becke et al. | 424/491 |

FOREIGN PATENT DOCUMENTS

WO 2008138590 A1 11/2008

OTHER PUBLICATIONS

Gilbert C, Boivin G. New reporter cell line to evaluate the sequential emergence of multiple human cytomegalovirus mutations during in vitro drug exposure. Antimicrob Agents Chemother. Dec. 2005;49(12):4860-6.*

Biron KK. Candidate anti-herpesviral drugs; mechanisms of action and resistance. In: Arvin A, Campadelli-Fiume G, Mocarski E, et al., editors. Human Herpesviruses: Biology, Therapy, and Immunoprophylaxis. Cambridge: Cambridge University Press; 2007. Chapter 68. Available from: http://www.ncbi.nlm.nih.gov/books/NBK47396/.*

Lilja AE, Mason PW. The next generation recombinant human cytomegalovirus vaccine candidates-beyond gB. Vaccine. Nov. 19, 2012;30(49):6980-90. Epub Oct. 3, 2012.*

"Mammalian Cell Culture" From Marquis CP. Biotechnology. vol. 1. Encyclopedia of Life Support Systems (EOLSSS). http://www.eolss.net/sample-chapters/c17/e6-58-01-04.pdf. Jun. 21, 2011.*

Hwang JS, Schilf R, Drach JC, Townsend LB, Bogner E. Susceptibilities of human cytomegalovirus clinical isolates and other herpesviruses to new acetylated, tetrahalogenated benzimidazole D-ribonucleosides. Antimicrob Agents Chemother. Dec. 2009;53(12):5095-101. doi: 10.1128/AAC.00809-09. Epub Sep. 28, 2009.*

Mobberley MA, Ryder TA, Hart H, Tyms AS. Fine structure of cells infected with human cytomegalovirus after treatment with 9-(1,3-dihydroxy-2-propoxymethyl)guanine. J Gen Virol. Jun. 1987;68 (Pt 6):1553-62.*

Prichard MN, Sztul E, Daily SL, Perry AL, Frederick SL, Gill RB, Hartline CB, Streblow DN, Varnum SM, Smith RD, Kern ER. Human cytomegalovirus UL97 kinase activity is required for the hyperphosphorylation of retinoblastoma protein and inhibits the formation of nuclear aggresomes. J Virol. May 2008;82(10):5054-67. Epub Mar. 5, 2008.*

Tandon R, Mocarski ES. Viral and host control of cytomegalovirus maturation. Trends Microbiol. Aug. 2012;20(8):392-401. doi: 10.1016/j.tim.2012.04.008. Epub May 23, 2012.*

Pepperl-Klindworth S, Frankenberg N, Plachter B. Development of novel vaccine strategies against human cytomegalovirus infection based on subviral particles. J Clin Virol. Aug. 2002;25 Suppl 2:S75-85.*

Becke S, Aue S, Thomas D, Schader S, Podlech J, Bopp T, Sedmak T, Wolfrum U, Plachter B, Reyda S. Optimized recombinant dense bodies of human cytomegalovirus efficiently prime virus specific lymphocytes and neutralizing antibodies without the addition of adjuvant. Vaccine. Aug. 31, 2010;28(38):6191-8. Epub Jul. 23, 2010.*

Irmiere A, Gibson W. Isolation and characterization of a noninfectious virion-like particle released from cells infected with human strains of cytomegalovirus. Virology. Oct. 15, 1983;130(1):118-33.*

(Continued)

*Primary Examiner* — Rachel B Gill
(74) *Attorney, Agent, or Firm* — Millen White Zelano and Branigan, PC

(57) ABSTRACT

The invention relates to the production of dense bodies (DB) and to a pharmaceutical composition containing DB.

18 Claims, 1 Drawing Sheet

(56) References Cited

OTHER PUBLICATIONS

Talbot P, Almeida JD. Human cytomegalovirus: purification of enveloped virions and dense bodies. J Gen Virol. Aug. 1977;36(2):345-9.*

International Search Report for PCT/EP2012/058094 dated Oct. 9, 2012.

Hwang, J-S. et al., "Identification of acetylated, tetrahalogenated benzimidazole d-ribonucleosides with enhanced activity against human cytomegalovirus," Journal of Virology, 2007, vol. 81, No. 21, pp. 11604-11611.

Buerger, I. et al., "A novel nonnucleoside inhibitor specifically targets cytomegalovirus DNA maturation via the UL89 and UL56 gene products," Journal of Virology, 2001, vol. 75, No. 19, pp. 9077-9086.

Pepperl, S. et al., "Dense Bodies of Human Cytomegalovirus induce both humoral and cellular Immune responses in the absence of viral gene expression," Journal of Virology, 2000, vol. 74, No. 13, pp. 6132-6146.

* cited by examiner

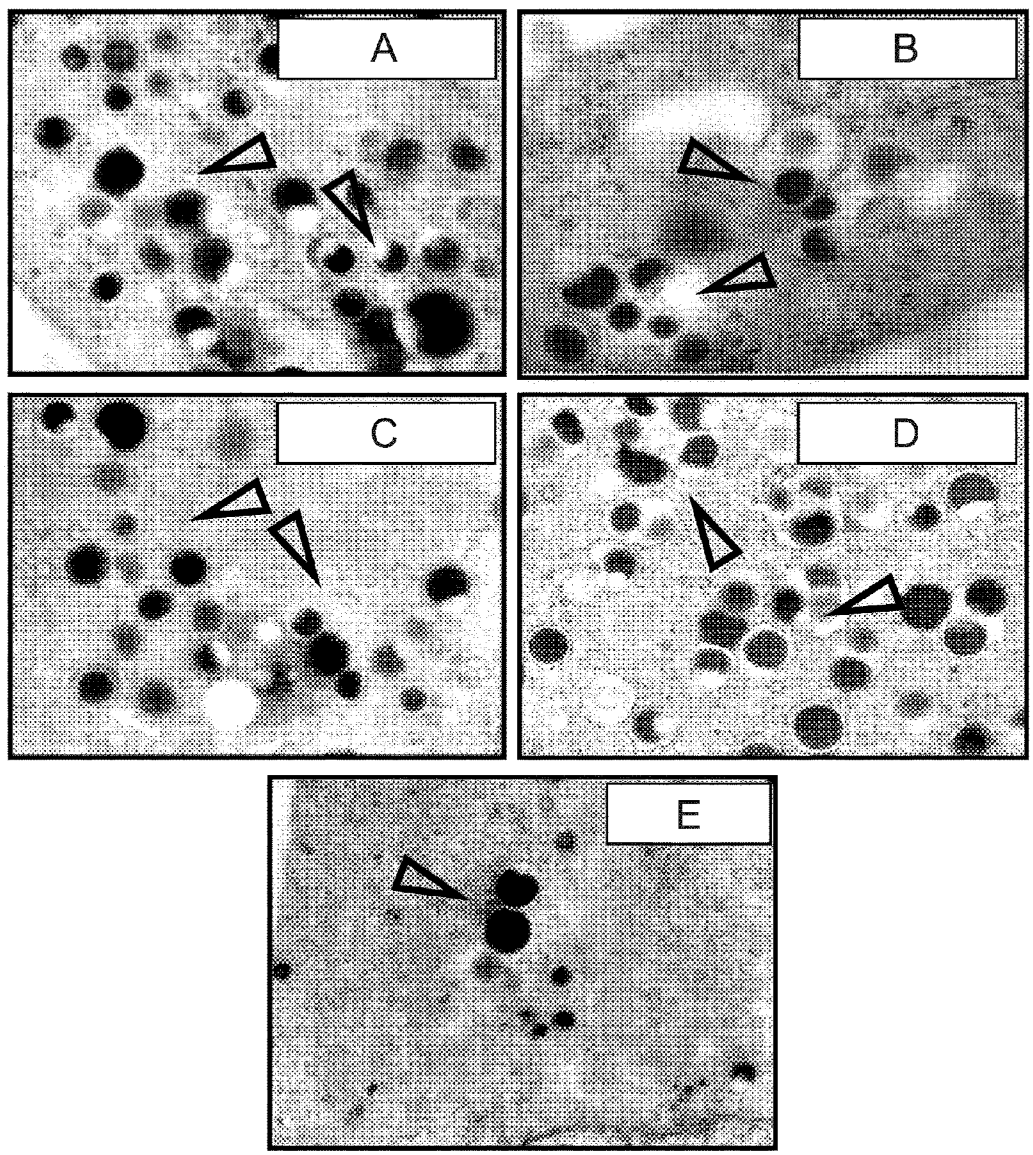
A
B
C
D
E

PRODUCTION OF DENSE BODIES (DB) FROM HCMV-INFECTED CELLS

This invention relates to the production of "Dense Bodies" (DB) as well as a DB-containing pharmaceutical composition.

The human cytomegalovirus (HCMV), which is also referred to as human herpes virus 5, is a sheathed, double-stranded DNA virus, which is part of the herpes viruses. HCMV is generally harmless for healthy adults. In pregnancy, however, the virus is shown to be especially dangerous and can even be life-threatening for unborn babies. Also, for humans with weakened immune systems, a fatal disease can develop from an infection with HCMV. Therefore, AIDS patients, transplant recipients, leukemia patients after stem cell transplants, and patients who are treated with cytostatic agents, etc., are at high risk.

In patients with weakened immune systems, virostatic agents, such as, for example, Ganciclovir, Foscarnet, Cidofovir and optionally also Aciclovir, are used in the case of an HCMV infection.

Also, work has already been underway for many years on the development of an inoculant or vaccine against HCMV. Thus, it was attempted, for example, to induce the desired immunity with weakened or attenuated live vaccines. However, only a limited protection could thus be achieved.

Another approach consists in performing a vaccination by means of so-called "Dense Bodies" (DB). In this connection, these are visible structures, which are derived from HCMV, in an electron microscope. DB are sheathed subviral particles in whose sheaths, which are derived from a cellular lipid membrane, viral glycoproteins are embedded. These viral proteins are present in the viral lipid membranes with higher probability in natural conformation. DB are formed in the cytoplasma of the infected cell, comparable to virus particles, and then are flushed from the cell. DB consist of up to 90% of their protein mass from the virally coded so-called pp65 protein (UL83). Also, in the D.B., i.a., the viral proteins pp150 (UL32), gH (UL75), gM (UL100) and gB (UL55) could be detected. Since DB do not contain any viral DNA nor any viral capsid, they are not infectious.

In the state of the art, it is described that DB, because of their antigenic properties that are similar to those of HCMV to a high degree, are suitable to act as an inoculant against or in the case of an HCMV infection. Such an inoculant has proven especially effective. Since DB are not infectious, the risk profile and the side effects are also to be rated as considerably less critical than in the case of a live vaccine. Thus, the DB-containing inoculant with the designation "VPM2001" is already undergoing clinical trials. The principle and the advantages of a vaccination with DB are described in, for example, WO 00/5372.

Since, in the normal infection cycle of HCMV, DB i) are formed only to a slight extent and are therefore available only to a limited extent, and ii) DB preparations can potentially be contaminated with infectious HCMV, there is the need for a method with which the formation of DB can be increased in a targeted manner and a contamination with infectious HCMV is prevented.

Reefschlaeger et al. (2001), Journal of Antimicrobial Chemotherapy 48, 757-767 and Buerger et al. (2001), Journal of Virology 75, 9077-9086, describe a substance with the designation BAY 38-4766, which is to increase the amount of DB formed.

Hwang et al. (2007), Journal of Virology 81, 11604-11611 and Hwang et al. (2009), Antimicrobial Agents and Chemotherapy 53, 5095-5101 describe benzimidazole-D-ribonucleosides, which also could be suitable for increasing the amount of DB that is formed.

The previously-described substances that are supposedly suitable for optimization of the DB formation have not proven of value in practice, however.

Against this background, the object of this invention is to provide additional substances that as an additive in the production of DB i) prevent DB preparations from becoming contaminated with infectious HCMV ii) increase the yield of DB within the framework of their production.

This object is achieved by using a substance that is selected from the following substances:

Another object underlying the invention is to provide a new method for the production of DB.

This additional object is achieved by a method that has the following steps: 1) Preparation of biological cells infected with the human cytomegalovirus (HCMV) in a suitable medium, and 2) Incubation of the infected biological cells with a substance, whereby the substance is selected from the above-mentioned substances (A) to (D).

The inventors have recognized that the above-identified substances are extraordinarily well-suited to produce DB. They were able to observe in particular that with HCMV-infected biological cells, such as, for example, primary fibroblasts, in the presence of these compounds, high concentrations of DB accumulate in the cytoplasm and are released into the medium. In this case, it has proven to be especially advantageous that the substances (A) to (D) prevent the assembly of intact virus particles in the cell nucleus and thus ensure that no infectious HCMV is flushed from the infected cells. The DB can therefore be easily isolated from the medium or the lysate of the infected cells without worrying about a contamination with infectious virus particles.

According to the invention, such biological cells that are permissive for HCMV are suitable for use in the method.

According to the invention, a "suitable medium" is defined as a conventional cell culture medium. In this case, the medium that is preferably to be used depends on the cell type that is used in each case. Suitable media are, e.g., Eagle's minimal essential medium (EMEM)+10% fetal calf serum (FCS)+2 mM of L-glutamine+1% penicillin/streptomycin (Pen/Strep; Penicillin G sodium 1,000 μg/ml; 0.85% streptomycin sulfate), EMEM+10% FCS+2 mM of L-glutamine+1 mM of sodium pyruvate (NaP)+1% non-essential amino acids+1% Pen/Strep or RPMI 1640 with 100 μg/ml of gentamicin; 5 U/ml of heparin; 50 μg/ml of endothelial cell growth factor; 15% human serum (seronegative for HCMV) and 12 μg/ml of Cibrobay, etc.

In this case, it is preferred according to the invention when the biological cells are primary cells, which are preferably selected from the group that consists of: human endothelial cells, human fibroblasts, human dendritic cells, human epithelial cells, and human macrophages.

This measure has the advantage that such cells are used that are permissive for HCMV and thus are especially suitable for production of DB.

It is also preferred when the incubation of the biological cells is carried out with the substance at a concentration of approximately 1 nmol/l up to approximately 100 μmol/l of medium.

This measure has the advantage that such a concentration range is selected that leads to especially good results according to the findings of the inventor. The exact concentrations depend on the biological cells that are used and the HCMV strain that is used for infection. They can be determined without difficulties in the individual case by one skilled in the art by simple titration series. Thus, the inventor could achieve optimal results with the substance (A) and human foreskin fibroblasts (HFF), which were infected with the HCMV strain AD169, at a concentration of 50 nmol/l. In the same batch, concentrations of 5 nmol/l, 500 nmol/l or 500 nmol/l for the substances (B), (C), and (D) led to optimal results. In the case of an incubation with human endothelial cells from the umbilical vein (HUVEC), which were infected with the HCMV strain TB40/E, concentrations of 300 nmol/l, 300 nmol/l, 3 μmol/l or 30 μmol/l for the substances (A), (B), (C) and (D) led to optimal results. When using HFF, which were infected with a clinical isolate of HCMV, in co-culture with non-infected HFF, concentrations of 300 nmol/l, 300 nmol/l, 3 μmol/l or 30 μmol/l also led to good results.

It is also preferred when the incubation is carried out over a period of 1 day to 14 days, preferably 3 to 10 days, and highly preferably 5 days.

This measure has the advantage that large enough amounts of DB are obtained in an incubation within the indicated time period.

According to the invention, it is also preferred when an isolation of the DB is carried out after the incubation of the biological cells with the substance.

This measure has the advantage that the DB can be provided in a form that makes possible a direct further processing, such as, for example, the formulation to create a vaccine. The isolation of the DB is carried out according to the method that is known to one skilled in the art. For example, the cell-free medium is centrifuged, and in this case, the DB are sedimented. The latter can then be easily separated from the supernatant.

Against this background, the invention also relates to a method for the production of a pharmaceutical composition, preferably a vaccine, which has the following steps: (1) Production of "Dense Bodies" (DB), (2) Preparation of the DB that is produced in Step (1), and (3) Formulation of the DB prepared in Step (2) in a pharmaceutically acceptable vehicle, whereby the production is carried out in Step (1) according to the above-described method according to the invention.

Pharmaceutically acceptable vehicles are generally known in the state of the art: they comprise, for example, binders, explosives, fillers, lubricating agents, as well as buffers, salts, and other substances that are suitable for formulation of pharmaceutical agents; cf. Rowe, E. et al. (2006), Handbook of Pharmaceutical Excipients, 5$^{th}$ Edition, Pharmaceutical Press; or Bauer et al. (1999), Lehrbuch der pharmazeutischen Technology [Textbook of Pharmaceutical Technology], 6$^{th}$ Edition, Wissenschaftliche Verlagsgesellschaft Stuttgart mbH. The contents of these publications are, by reference, components of this application.

In the production of a vaccine, adjuvants can also be provided that bring about the enhancement of the immune response. In this case, these can be oil-water mixtures, lipopolysaccharides, aluminum hydroxide, etc. Adjuvants are described comprehensively in the state of the art.

Against this background, the invention also relates to a pharmaceutical composition, preferably a vaccine, which is produced according to the above-described method.

The features, properties and advantages described in reference to the use according to the invention and the method for production of DB according to the invention apply to an equal extent to the method for production of a pharmaceutical composition according to the invention and to the pharmaceutical composition according to the invention.

Subsequently, preferred embodiments of the invention are described that are purely illustrative and do not limit the scope of the invention. In this case, reference is made to the accompanying figure, in which the following is depicted:

FIG. 1 shows electron-microscopic images of cells incubated with the substances (A), (B), (C) and (D) and previously with HCMV-infected cells, which in comparison to untreated cells (E) accumulate large amounts of DB (arrows) in their cytoplasm.

EMBODIMENTS

1. Substances (A) to (D) According to the Invention

The synthesis of substance (A) (4S)-{8-fluoro-2-[4-(3-methoxyphenyl)-1-piperazinyl]-3-[2-methoxy-5-(trifluoromethyl)-phenyl]-3,4-dihydro-4-quinazolinyl}acetic acid is described in detail in WO 2004/096778, Embodiments 14 and 15 on pages 72 and 73.

The synthesis of the substance (B) N-{1-methyl-2-[(4-(5-methyl-pyridin-2-yl)-piperazin-1-yl)carbonyl]-1H-imidazol-4-yl}-N'-[4-(trifluoromethoxy)phenyl]urea is described in detail in WO 2006/089664, Embodiment 2 on pages 39 and 40.

The synthesis of the substance (C) 1-[6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid is described in detail in WO 2007/090579, Embodiment 47 on pages 96 and 97.

The synthesis of substance (D) N-{3-[({4-[5-(6-aminopyridin-2yl)-1,2,4-oxadiazol-3-yl]phenyl}sulfonyl)amino]-5-fluorophenyl}-1-cyanocyclopropane carboxamide is described in detail in WO 2007/101573, Embodiment 1, page 49.

The contents of the preceding documents WO 2004/096778, WO 2006/089664, WO 2007/090579 and WO 2007/101573, in particular with respect to the identified synthesis descriptions, are, by reference, components of this disclosure.

2. Production of "Dense Bodies" (DB)

2.1 Production in Fibroblasts Infected with the HCMV Strain AD169

Human foreskin fibroblasts ("human foreskin fibroblasts, HFF") were added in an amount of $1\times10^6$ cells per flask in 5 T75-cell culture flasks on the day before the infection. The HCMV strain AD169 was prepared as a frozen, cell-free virus preparation that was obtained from cells that were present in a late stage of infection. The substances (A), (B), (C), and (D) according to the invention were provided as stock solutions of 50 mmol/l each in DMSO.

The stock solutions were diluted 1:1000 to a final concentration of 50 μmol/l. The solutions were further diluted as follows: A: 1:1000 (50 nmol/l) 12 μml in 12 ml of MEM; B: 1:10,000 (5 nmol/l) 1.2 μml in 12 ml of MEM; C: 1:100 (500 nmol/l) 120 μml in 12 ml of MEM; D: 1,100 (500 nmol/l) 120 μml in 12 ml of MEM.

The HFF cells were incubated for one hour with the virus preparation at a m.o.i. ("multiplicity of infection") of ≥≥1 TCID 50/cell (1:20 dilution). Then, the virus supernatant was removed, and an incubation of the infected cells was carried out with the substances according to the invention at the following concentrations: A: 50 nmol/l; B: 5 nmol/l; C: 500 nmol/l; D: 500 nmol/l.

The cells were incubated for 5 days, whereby a renewal of the substance-containing medium was performed after the first and fourth days. After the incubation, the infected cells were examined by electron microscope in the formation of DB.

The result is shown in the attached FIG. 1. In this connection, it is shown that all cells treated with the substances (A), (B), (C) and (D) according to the invention accumulated high concentrations of DB (arrows), while the untreated cells (E) accumulated virtually no DB in their cytoplasm. The DB are identified with arrowheads. Moreover, no single infectious virus particle was to be found in the cytoplasm of the treated cells, while corresponding particles were to be detected in relatively large numbers in the cytoplasm of untreated cells.

2.2 Production in Endothelial Cells Infected with the HCMV-Strain TB40/E

In another experiment, human endothelial cells from the umbilical vein (HUVEC) were infected with the HCMV strain TB40/E, which was isolated from cells in a late stage of infection. The experimental design corresponds to the one shown under 2.1, whereby the incubation of cells was carried out at the following concentrations of the substances according to the invention: A: 300 nmol/l; B: 300 nmol/l: C: 3 μmol/l; D: 30,000 μmol/l.

In the examination by electron microscope, a strong concentration of DB in the cytoplasm of the infected cells, which were incubated with the substances (A), (B), (C), and (D) according to the invention, was also shown. In the control batch (E), only a few DB could be identified. Analogously to the observations described in 2.1, also no virions could be detected in the cytoplasm of the treated batch.

2.3 Production in Fibroblasts, Infected with a Clinical HCMV Isolate, in Co-Culture with Non-Infected Fibroblasts HFF were infected with a clinical HCMV isolate, which was isolated from cells in a late stage of infection, as further described above under 2.1. The infected HFF were co-cultivated with non-infected HFF in mini-trays (3,000 cells/recess). Three different ratios of infected/non-infected cells were produced: undiluted; 1:2 diluted; 1:4 diluted. The substances according to the invention were incubated with the cells at the following concentrations: A: 300 nmol/l; B: 300 nmol/l; C: 3 μmol/l; D: 30 μmol/l.

After 5 days of incubation at 37° C., the electron-microscopic study was carried out. In this case, it was shown that in the batches in which the highest proportions of infected cells were present, i.e., the "undiluted" batches, the cells accumulated very large amounts of DB in their cytoplasm after incubation with the substances according to the invention. The greater the dilution with non-infected cells, the fewer DB accumulated in the cytoplasm. In the control batch without a substance according to the invention, only very few DB could be identified. Moreover, the ejection of infectious particles from the cell nucleus was prevented in turn by the addition of the substances according to the invention.

3. Isolation of the Dense Bodies

The isolation is described in detail in the state of the art, for example in Pepperl et al. (2000), Journal of Virology 74, 6132-6146, and in Irmiere, A. and W. Gibson (1993), Virology 130, 118-133. The contents of the above-mentioned publications are, by reference, components of this application.

Accordingly, the particles are purified as follows from the culture medium of the infected cells: the infected cells are scraped off 6 days after the infection from the bottom of the cell culture flask and are resuspended in the medium. The suspension is centrifuged at low speed, for example at 1,500 g for 4°, 10 minutes. The cell-free medium that is obtained is added to a potassium tartrate-glycerol gradient, produced in 0.05 ml of Tris HCl, pH 7.4, 0.1 M of NaCl (TN buffer; Talbot and Almeda, 1977), and centrifuged at 40,000 rpm for 4°, 15 minutes with use of a Beckman Rotor SW41 and a Sorvall Ultracentrifuge OTD-50 at low acceleration and in the "raking" mode. The DB-containing band was identified in the gradient by its characteristic light-scattering property. The band was drawn off by suction with use of a 32-gauge needle through the wall of the centrifuging tube. Optionally, the DB can be further purified by renewed corresponding sedimentations or extended centrifuging processes up to an equilibrium, i.e., for 18 hours, with use of the same gradient and centrifuging conditions.

4. Result

The inventors could show that with the substances (A), (B), (C), and (D), extraordinarily effective large amounts of Dense Bodies could be produced, which can be used, for example, after isolation and purification as a vaccine are completed. It is especially advantageous that by means of the above-mentioned substances, DB at high purity can be isolated.

The invention claimed is:

1. A method for preparing dense bodies, comprising (1) preparing isolated biological cells that are infected with human cytomegalovirus (HCMV) in a medium, and (2) incubating the infected biological cells with one of the following substances (A), (B), (C) or (D) at a concentration of the substance (A), (B), (C) or (D) of approximately 1 nmol/l to approximately 1 μmol/l:

substance (A), which is (4S)-{8-fluoro-2-[4-(3-methoxyphenyl)-1-piperazinyl]-3-[2-methoxy-5-(trifluoromethyl)-phenyl]-3,4-dihydro-4-quinazolinyl}acetic acid;

substance (B), which is N-{1-methyl-2-[(4-(5-methylpyridin-2-yl)-piperazin-1-yl)carbonyl]-1H-imidazol-4-yl}-N'-[4-(trifluoromethoxy)phenyl]urea;

substance (C), which is 1-[6-fluoro-8-methoxy-3-({[2-methyl-4-(trifluoromethoxy)benzyl]amino}carbonyl)-4-oxo-1-(2,2,2-trifluoroethyl)-1,4-dihydroquinolin-7-yl]piperidine-4-carboxylic acid; or substance (D), which is N-{3-[({4-[5-(6-aminopyridin-2yl)-1,2,4-oxadiazol-3-yl]phenyl}sulfonyl)amino]-5-fluorophenyl}-1-cyanocyclopropane carboxamide, and then (3) isolating the resultant dense bodies from the cell supernatant without lysing the cells.

2. The method according to claim 1, wherein the biological cells are primary cells.

3. The method according to claim 1, wherein the biological cells are human endothelial cells, human fibroblasts, human dendritic cells, human epithelial cells, or human macrophages.

4. The method according to claim 1, wherein (2) is carried out at a concentration of the substance (A), (B), (C) or (D) of approximately 1 nmol/l to approximately 50 nmol/l.

5. The method according to claim 1, wherein (2) is carried out over a period of 1 day to 14 days.

6. The method according to claim 1, wherein in (3), the dense bodies are separated from said medium by centrifuging.

7. A method for preparing a pharmaceutical composition, comprising mixing together a pharmaceutically acceptable carrier and dense bodies that have been prepared by the method according to claim 1.

8. The method according to claim 1, wherein (2) is carried out over a period of 3 days to 10 days.

9. The method according to claim 1, wherein (2) is carried out over a period of 5 days.

10. The method according to claim 1, wherein in (2) substance (A) is incubated with the infected biological cells.

11. The method according to claim 1, wherein in (2) substance (B) is incubated with the infected biological cells.

12. The method according to claim 1, wherein in (2) substance (C) is incubated with the infected biological cells.

13. The method according to claim 1, wherein in (2) substance (D) is incubated with the infected biological cells.

14. The method according to claim 1, wherein the biological cells are permissive for HCMV.

15. The method according to claim 1, wherein the biological cells are from a stable cell line.

16. The method according to claim 1, wherein the biological cells are human foreskin fibroblasts or human endothelial cells from the umbilical vein.

17. The method according to claim 1, wherein (2) is carried out at a concentration of the substance (A), (B), (C) or (D) of approximately 5 nmol/l to approximately 500 nmol/l.

18. The method according to claim 1, wherein (2) is carried out at a concentration of the substance (A), (B), (C) or (D) of approximately 3 nmol/l to approximately 300 nmol/l.

* * * * *